(12) United States Patent
Nelson (10) Patent No.: US 6,349,128 B1
(45) Date of Patent: Feb. 19, 2002

(54) METHOD AND DEVICE USING X-RAYS TO MEASURE THICKNESS AND COMPOSITION OF THIN FILMS

(75) Inventor: Keith A. Nelson, Newton, MA (US)

(73) Assignee: Philips Electronics North America Corporation, New York, NY (US)

(*) Notice: Subject to any disclaimer, the term of this patent is extended or adjusted under 35 U.S.C. 154(b) by 0 days.

(21) Appl. No.: 09/561,508

(22) Filed: Apr. 27, 2000

(51) Int. Cl.⁷ .............................................. G01N 23/223
(52) U.S. Cl. ........................................... 378/44; 378/50
(58) Field of Search ..................... 378/44–50

(56) References Cited

U.S. PATENT DOCUMENTS

| | | | |
|---|---|---|---|
| 3,961,197 A | 6/1976 | Dawson | 250/493 |
| 4,710,030 A | 12/1987 | Tauc et al. | 356/432 |
| 4,724,536 A * | 2/1988 | Oba | 378/45 |
| 5,546,811 A | 8/1996 | Rogers et al. | 73/800 |
| 5,633,711 A | 5/1997 | Nelson et al. | 356/318 |
| 5,812,261 A | 9/1998 | Nelson et al. | 356/318 |

OTHER PUBLICATIONS

"X–ray Fluorescence Correlation Spectroscopy for Studying Particle Dynamics in Condensed Matter", by Jin Wang et al, American Institute of Physics, Tenth U.S. National Conference, 1997, p. 158.

"Coherent Spectroscopy Throughout the Brillouin Zone", Workshop on Scientific Applications of Coherent X–Rays, Feb. 12, 1994 by Keith A. Nelson, Dept. of Chemistry, MIT.

Coherent X–Ray Generation, http://www.eecs.umich.edu/CUOS/research/frameHighlight97_1.html.

"X–Ray Fluorescence Spectroscopy", http://www.surface-science.com/xrf.html.

"Ultrafast Structural Dynamics in InSb Probed by Time–Resolved X–ray Diffraction", by A.H. Chin et al, pp. 401–403.

* cited by examiner

Primary Examiner—Craig E. Church (57) ABSTRACT

A method and apparatus for measuring a property (e.g., thickness or composition) of at least one film in a sample (e.g., a multilayer film stack contained in a microelectronic device) is disclosed. The method features the steps of generating a coherent x-ray pulse, delivering the coherent x-ray pulse to a region on the sample to generate a signal beam, detecting the signal beam to generate an electrical signal, and analyzing the electrical signal to determine the property (e.g., thickness) of the film.

37 Claims, 6 Drawing Sheets

METHOD AND DEVICE USING X-RAYS TO MEASURE THICKNESS AND COMPOSITION OF THIN FILMS

FIELD

This invention relates to an x-ray-based method and apparatus for measuring thickness and/or composition of samples; more particularity, the invention relates to the use of coherent: x-rays generated using short, optical pulses to measure properties of thin films contained in multi-layer samples.

BACKGROUND

Thin films of dielectric (e.g., polymer, oxide) and conducting (e.g., metal) materials are used in a range of microelectronic, optical, and biomedical devices. A microprocessor, for example, contains multiple layers of metal and oxide thin films deposited on a semiconducting material (e.g., a silicon substrate). Thickness and compositional variations in these films can modify their electrical and mechanical properties, thereby affecting the performance of the microprocessor. Accordingly, film thickness and composition are often monitored as quality-control parameters during and/or after the microprocessor's fabrication.

Several film measurement techniques, such as optical ellipsometry, reflectometry, Impulsive Stimulated Thermal Scattering (ISTS), and x-ray fluorescence (XRF) are known to measure oxide and metal films during fabrication of a microprocessor. In XRF, a beam of x-rays is generated and collimated using conventional x-ray optics; in this case, the beam that irradiates the sample typically has a diameter on the order of 1 cm.

Alternatively, the collimated x-ray beam can be passed through a mask that spatially filters it to generate a beam having a diameter of a few hundred microns. The disadvantage of this technique, of course, is that the filtered x-ray beam has a significantly lower power than the x-ray beam before the mask.

Techniques to generate X-rays using laser-based methods are also known. In one such technique, a high-peak-power femtosecond laser pulse is focused on an atomic gas. The interaction of the laser light and atomic gas creates emissions of coherent high-order harmonics. This essentially changes the femtosecond pulse's energy from the visible spectrum region to the soft-x-ray spectrum region. In addition, X-ray laser sources are also know in that produce coherent radiation.

The inventor has discovered significant advantages in the use of coherent x-rays in performing measurements as compared to conventional measurement and x-ray fluorescence techniques. These benefits and advantages overcome numerous shortcomings of conventional XRF, as discussed below.

SUMMARY

In the present invention, the use of coherent x-ray emissions provides improvements over conventional measurement and x-ray fluorescence techniques. Coherence refers to the correlation between propagation characteristics of a signal at points separated in space, or in time, or both.

The advantages of the present invention include the use of high intensity coherent x-rays. As discussed above, the spatial filter, i.e., the mask, used in conventional XRF significantly limits the x-ray power output. Moreover, even with such filtering, the XRF beam typically has a diameter on the order of 1 cm. In the present invention, the coherent x-rays allow for extremely small spot sizes to be measured (e.g., on the order of a few microns or even well under 1 micron) without the need for any spatial filtering.

In addition, the spatial coherence of such x-rays provides advantages in measuring thickness and compositions. Such coherent x-rays, for example, allow measurements to be made at longer distances to sample than conventional XRF. In measurements in which beams are crossed (e.g., ISTS measurements), coherent x-rays allow for greater spatial resolution. Depending on the focussing optics, either the spot sizes or fringe spacing resulting from the crossed x-ray beams can be in the submicron range.

Also, the short pulse duration of such coherent radiation allows for time-resolved measurements, or measurements as a function of time delay between two pulses, e.g., an x-ray pulse and an optical pulse or two x-ray pulses. For example, one pulse excites electrons, and another pulse (preferably a different wavelength) is absorbed by the excited states to produce a still higher-lying state that fluoresces. It is noted that the delay between the pulses is important because the initially excited levels are short-lived. Combined x-ray and visible excitation pulses may also be useful in this respect. For example, the x-rays excite core electrons, and then the visible pulses (readily available and synchronizable since these visible pulses are also used to generate the coherent x-rays) are used to make measurements (time-resolved or otherwise) on the excited electrons or on the "holes" left behind (the latter includes optical or x-ray transitions that promote electrons from a filled core level into the core level that was vacated by the first x-ray pulse). Such measurements add selectivity for particular species, since now more than one transition frequency and also a decay lifetime can be matched.

Another advantage discovered by the inventor is based on the simultaneous availability of multiple x-ray wavelengths. For example, different x-ray harmonics may be selected from two supply fibers (as discussed below) or from a single fiber. Typically a single fiber output may consist of a series of nearby harmonics (e.g. harmonics #100, 101, 102, 103, 104, 105 . . . ). This allows for a "comb" of evenly spaced frequencies and nearly evenly spaced wavelengths. Having various wavelengths available in this form enables several useful measurements, as follows:

(1) Comparison between XRF emission generated from two or more wavelengths may be used as a basis for discrimination between different materials. In general, an x-ray "excitation spectrum" (intensity of fluorescence at a fixed wavelength measured as a function of excitation wavelength) may be collected.

(2) Soft x-ray interferometry/reflectometry. This is useful for ultrathin films and for films that are opaque to visible light. In this regard, in spectroscopic and variable-angle interferometry multiple wavelengths and angles for coherent high input are used. As the angle of incidence is varied, the optical path length reaches an integer multiple of each wavelength in succession, i.e., it depends on the peculiarity of the evenly spaced harmonic wavelength spectrum.

(3) Correlation measurements involving different wavelengths. For example, first assuming that wavelength 1 promotes core electrons from material 1, this leads to fluorescence when those electrons return to their core levels. Also, assume that wavelength 2 does the same for material 2. The question is whether wavelength 2 increases fluorescence at wavelength 1 when both are applied. If the materials 1 and 2 are well mixed, this is the case. If the materials 1 and 2 are in immiscible clusters or domains whose sizes exceed the electron diffusion length, this is not the case. This embodiment is useful for solid-state alloys or concrete, for example.

Another question is whether there is a time delay when performing such correlation measurements. In this embodiment, measurement of the average separation of the materials can be made (e.g., adhesion and delamination properties can be measured). This separation can either be due to incomplete mixing or because the materials 1 and 2 are in a multilayer assembly and there's a film or an interface between them (e.g., an electron transport across the materials).

In view of these discoveries, it is an object of the invention to provide a method and apparatus for measuring a property of thin films using coherent x-rays generated using short, optical pulses.

In one aspect, the invention provides a method and apparatus for measuring a property (e.g., thickness or composition) of at least one film in a sample (e.g., a multilayer film stack contained in a microelectronic device). This embodiment includes the steps of: i) generating an optical pulse; ii) focussing the optical pulse onto or in a material to generate a coherent x-ray pulse; iii) delivering the coherent x-ray pulse to a region on the sample to generate a signal beam; iv) detecting the signal beam to generate an electrical signal; and v) analyzing the electrical signal to determine the property (e.g., thickness) of the film.

In some cases, the coherent x-ray pulse could be generated directly from a laser source, without the need for steps (i) and (ii).

In a preferred embodiment, the optical pulse has duration of 5 picoseconds or less, and is generated with a laser that includes titanium:sapphire as a lasing medium. To generate the coherent x-ray beam, the optical pulse can be focused into a gas-containing container or into an optical fiber that includes at gas-containing region. The gas used in the fiber or container typically includes argon, helium, hydrogen, or nitrogen. X-ray pulses generated by this method typically have a duration that is less than twice the duration of the optical pulse, can be focused to extremely small spot sizes (e.g., on the order of a few microns or less), and have very low spatial divergence.

In one embodiment, the coherent x-ray pulse initiates fluorescence (e.g., optical or x-ray fluorescence) in the sample that forms the signal. In this case, the signal is not necessarily coherent, e.g., it can be incoherent fluorescence. The x-ray-induced fluorescence reaches a detector and generates an electrical signal having properties determined by the fluorescence intensity and energy that can be determined by analyzing the signal beam. In one case, the fluorescence intensity is compared to a mathematical model (e.g., a look-up table or function) that relates fluorescence intensity to the film's thickness. In addition to intensity, the fluorescence photon energy can be compared to a similar mathematical model that relates fluorescence energy to the film's composition.

In another embodiment, one or more x-ray beams are delivered to the sample to generate an acoustic response, such as an acoustic wave or pulse. For example, two x-ray beams can be spatially overlapped on the sample surface to form an interference pattern. The sample absorbs the interference pattern to launch acoustic waves that propagate in the plane of the film. Then an optical or x-ray probe beam irradiates the acoustic waves to generate the signal beam. In one case, the acoustic waves diffract a portion of the probe beam to form a signal beam modulated at a frequency that matches the frequency of the acoustic waves. The detecting step then further includes measuring and analyzing the diffracted portion of the probe beam to determine its frequency. The frequency can then be analyzed with a mathematical model to determine a thickness of the film.

Alternatively, a single x-ray beam can irradiate the sample's surface to initiate an acoustic wave or pulse that propagates perpendicular to the plane of the film. Here, a portion of the probe beam reflects off the acoustic response, and is detected and analyzed to determine a time-dependent feature (e.g., a series of echoes spaced in time). In this case, the time-dependent feature is analyzed to determine a thickness of the film.

The present invention has many advantages. In general, the invention features a non-contact measurement technique that simultaneously and effectively measures the thickness and composition of multiple thin films contained in a multi-layer structure. These properties can then be used to control a fabrication process (e.g., fabrication of a microelectronic device).

The invention features all the advantages of x-ray metrology, for example, each measurement is non-contact and remote (in the present invention, the measurement system can be as far as 10 cm or more from the sample). In addition, the invention can also make measurements over very small (sub-micron) regions, which can not be performed by known x-ray metrology. More particularly, this feature permits measurement of very small test areas (typically 100×100 microns) and possibly even actual features (typically 0.2 microns or less) contained in microelectronic devices. Other properties besides film thickness (e.g. composition) may also be measured more precisely through the use of the invention.

Other advantages include short pulse duration, which enables measurement of time-dependent dynamics of a sample. For example, x-ray-based measurement such as diffraction can be performed with a time resolution on the order of the pulse duration. In addition, the high peak intensity of the coherent x-rays enables measurements based on nonlinear responses of the sample (e.g. two-photon absorption and resultant fluorescence or other responses, harmonic generation, transient changes in absorption or refractive index in either the x-ray or other spectral region). The high spatial coherence enables small, micron-sized measurement area and additionally enables interference-based measurements, such as four-wave mixing, and facilitates alignment and measurement of a reflected beam or other coherent signals.

Other features, aspects, and advantages of the invention follow from the following detailed description, and from the claims.

BRIEF DESCRIPTION OF DRAWINGS

The features and advantages of the present invention can be understood by reference to the detailed description of the preferred embodiments set forth below taken with the drawings, in which.

DETAILED DESCRIPTION

Figure 1:
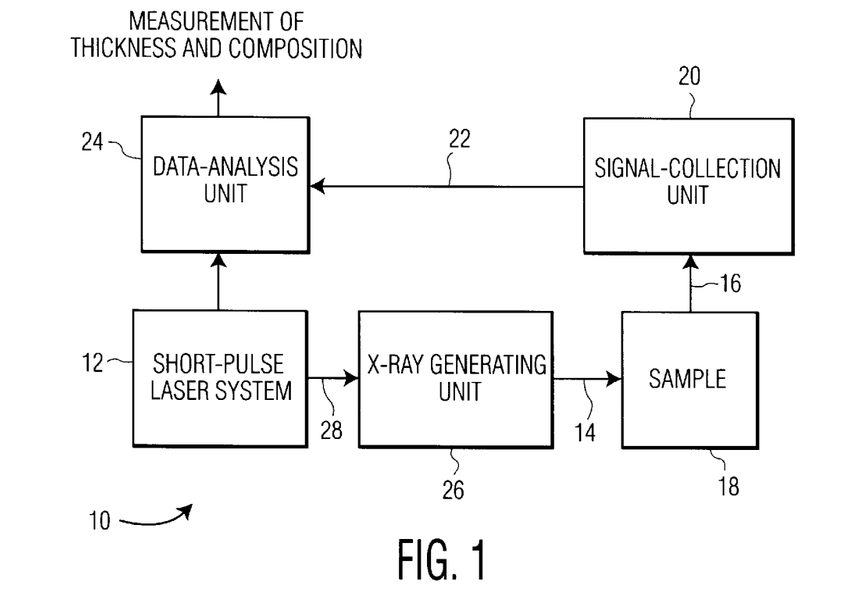
FIG. 1 is a schematic block drawing of an apparatus for measuring a sample with a coherent x-ray pulse.

Referring to FIG. 1, an x-ray-based system 10 measures a thickness, composition or other property of a sample 18. The sample 18 may contain multiple thin film layers. Preferably, the system 10 uses a short-pulsed laser system 12 to generate a coherent x-ray beam 14. During operation, the x-ray beam 14 irradiates the sample 18 to induce x-ray fluorescence 16 having an intensity and energy that are related, respectively, to the film thickness and composition. A signal-collection unit 20 collects the fluorescence 16 and, in response, generates an electrical signal 22 (e.g., a digitized spectrum) that indicates a thickness and/or composition of a film (or multiple films) in the sample 18. A data-analysis unit 24 receives and processes the electrical signal 22 to determine the thickness and/or composition of the sample 18.

The short-pulsed laser system 12 generates an optical pulse 28 having a duration on the order of 100 femtoseconds (i.e., 100×10–15 seconds) and energy on the order of 1 millijoule. The laser system 12 includes both a laser source and an optical amplifier (not shown). Preferably, both the laser source and the optical amplifier use a gain medium of titanium:sapphire that is irradiated with a Nd:YAG laser having an output that is frequency-doubled to 532 nm. Other types of active laser mediums media, such as crystal, gas, glass, liquid or semiconductor (e.g., diode, Nd:YAG and fiber), may also be used to generate the short pulses.

Once generated, an x-ray-generating unit 26 receives and processes the laser pulse 28 to generate the coherent, x-ray pulse 14. Generally, the resultant x-ray pulse 14 has a duration comparable to or shorter than the optical pulse (100 femtoseconds) and a very low divergence because of its short wavelength and consequent long Rayleigh range.

Figure 2:
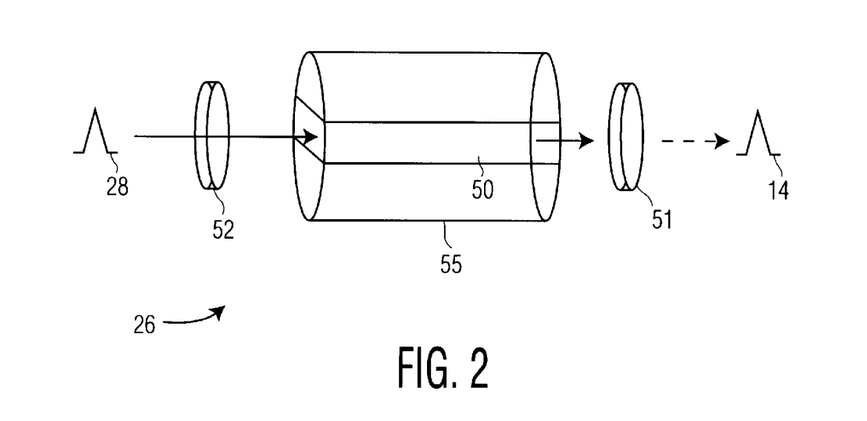
FIG. 2 is a schematic side view of a laser pulse irradiating a gas-filled chamber to generate an x-ray pulse.

Referring to FIG. 2, the x-ray generating unit 26 features a lens 52 that focuses the laser pulse 28 into a gas-filled cell 50 contained in a glass fiber 55. The cell 50 generates coherent, high-order harmonic radiation that passes through a filter 51, resulting in the x-ray pulse 14. At this point the x-ray pulse 14 is highly coherent and has low spatial divergence, allowing it to be delivered directly to the sample 18 to induce fluorescence.

In a typical embodiment, the fiber 55 is positioned within a few centimeters of the sample 18. This allows the x-ray pulse 14 to be delivered without passing through any additional delivery optics.

Figure 3A:
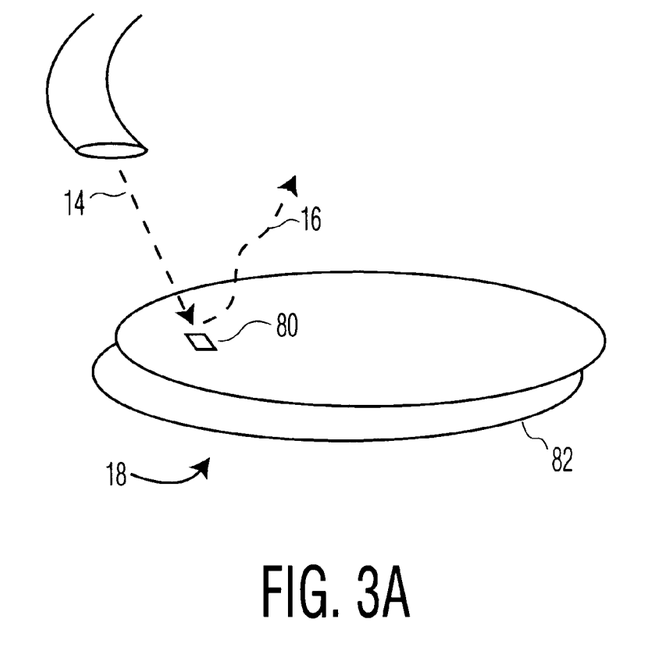
FIG. 3A is a schematic side view of a semiconductor wafer featuring a semiconductor device being measured with the apparatus of FIG. 1.
Figure 3B:
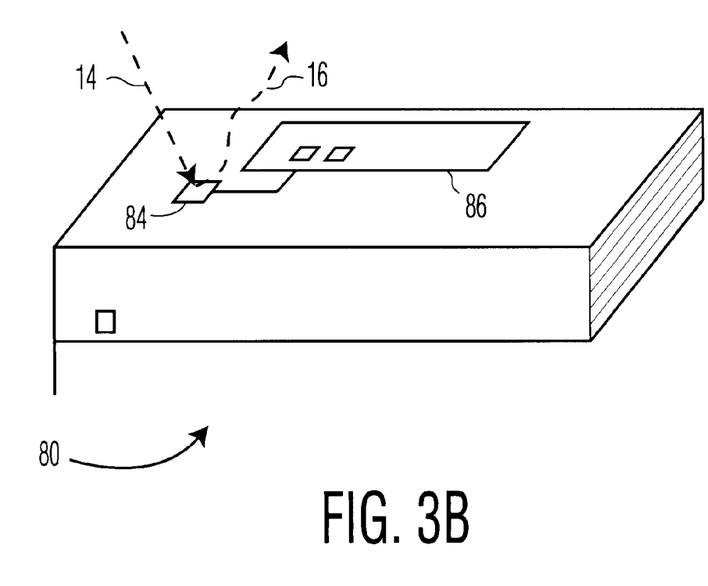
FIG. 3B is a schematic side view of the semiconductor device of FIG. 3A.

Referring to FIGS. 3A and 3B, the x-ray pulse 14 irradiates the sample 18 to generate X-ray fluorescence 16. The sample 18 includes a semiconductor wafer 82 that may be patterned to include multiple semiconductor devices 80. Each semiconductor device 80 features a measurement region 84, such as a test region or bond pad proximal to active region 86 of the semiconductor device 80. Thickness variations in the metal films contained in the bond pad can modify its electrical and mechanical properties, thereby affecting the performance of the semiconductor device 80. Thickness measurements can therefore be analyzed to control the quality of semiconductor devices during the fabrication process.

In typical applications, thin films of metals and metal alloys are deposited on silicon wafers and used as electrical conductors, adhesion-promoting layers, and diffusion barriers. For example, metal films of copper, tungsten, and aluminum are used as electrical conductors and interconnects; titanium and tantalum as adhesion-promoting layers; and titanium:nitride and tantalum:nitride as diffusion barriers.

Figure 4:
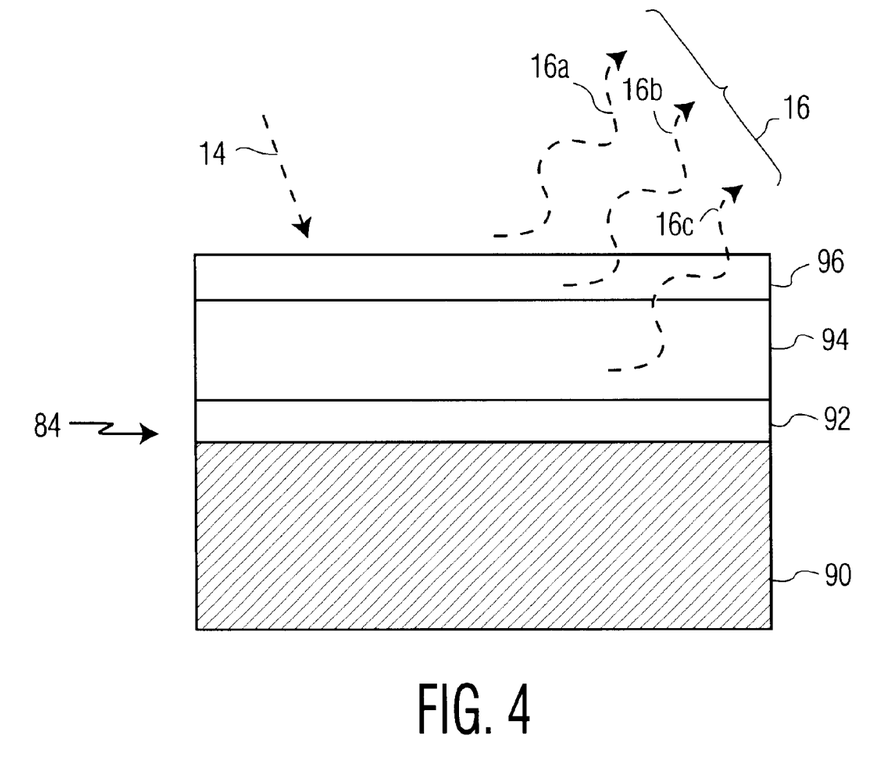
FIG. 4 is a schematic, cross-sectional view of the semiconductor device of FIG. 3A being measured with the X-ray beam.

FIG. 4 shows in more detail how the x-ray pulse 14 induces X-ray fluorescence 16 in the measurement region 84 of the semiconductor device 80. The measurement region 84 is composed of a metal adhesion-promoting layer 92, a metal conducting layer 94, and a metal anti-reflection layer 96, each disposed sequentially on a silicon substrate 90. During operation, the x-ray beam 14 irradiates the measurement region 84 and is partially absorbed by each layer 92, 94, 96. Absorption of the x-rays 14 induces x-ray fluorescence 16, composed of fluorescence 16a–c from each layer, that radiates outward. For the buried layers 92, 94, this fluorescence is partially absorbed by overlying metal layers. For example, the anti-reflection layer 96 may absorb fluorescence from both the conducting layer 94 and the adhesion-promoting layer 92.

Figure 5A:
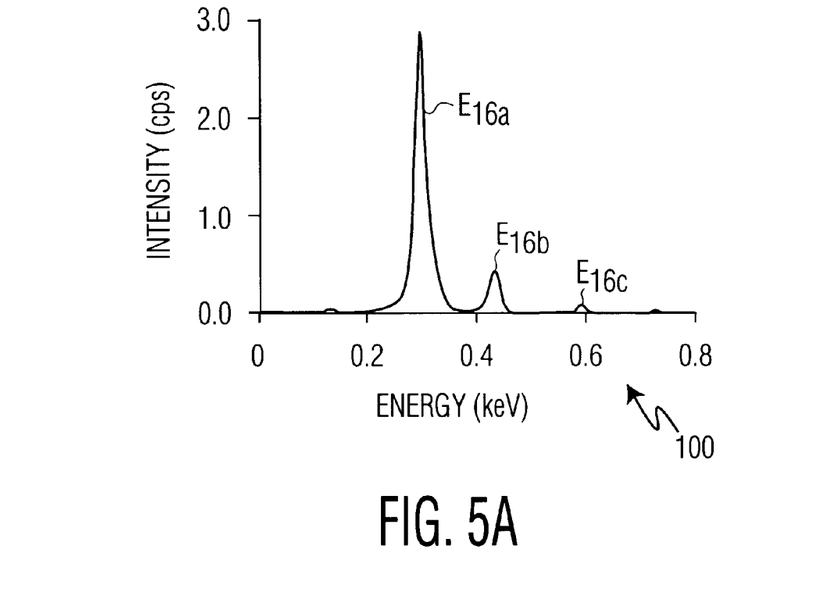
FIG. 5A is a plot of x-ray-induced fluorescence intensity as a function of x-ray fluorescence photon energy.
Figure 5B:
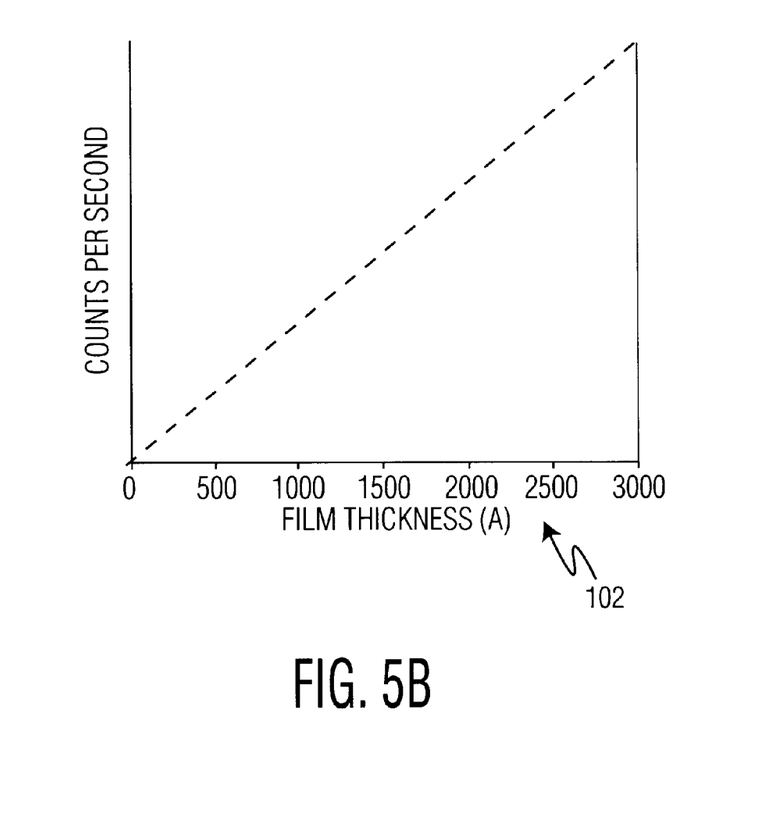
FIG. 5B is plot of x-ray-induced counts measured from a thin film as a function of film thickness.

Referring again to FIG. 1, the signal-collection unit 20 receives the fluorescence 16 after it leaves the leaves the measurement region 84. For example, the signal-collection unit 20 may include x-ray dispersing optics that disperse and sort x-rays according to their energy to generate an x-ray spectrum. Such a spectrum is shown in FIG. 5A. It typically includes peaks, in this case labeled $E_{16a}$, $E_{16b}$, and $E_{16c}$ that correspond to fluorescence 16a, 16b, 16c emitted, respectively, from the adhesion-promoting layer 92, the conducting layer 94, and the anti-reflection coating layer 96. Each peak in the spectrum has a corresponding intensity that depends on the number of "counts" detected at that particular energy. The number of counts increases with the film thickness. For example, FIG. 5B shows a correlation plot 102 indicating how the number of counts depends on the film thickness in a linear fashion. Correlation lots like that shown in FIG. 5B are determined prior to making an actual measurement and are contained (e.g., stored in a computer memory) in the data-analysis unit 24 of FIG. 1. A correlation plot is generated beforehand using a set of calibration samples having systematically varying thickness measured, e.g., with a secondary technique such as SEM. During an x-ray measurement, the number of counts is compared to the correlation plot 102 to determine the film's thickness.

Figure 7:
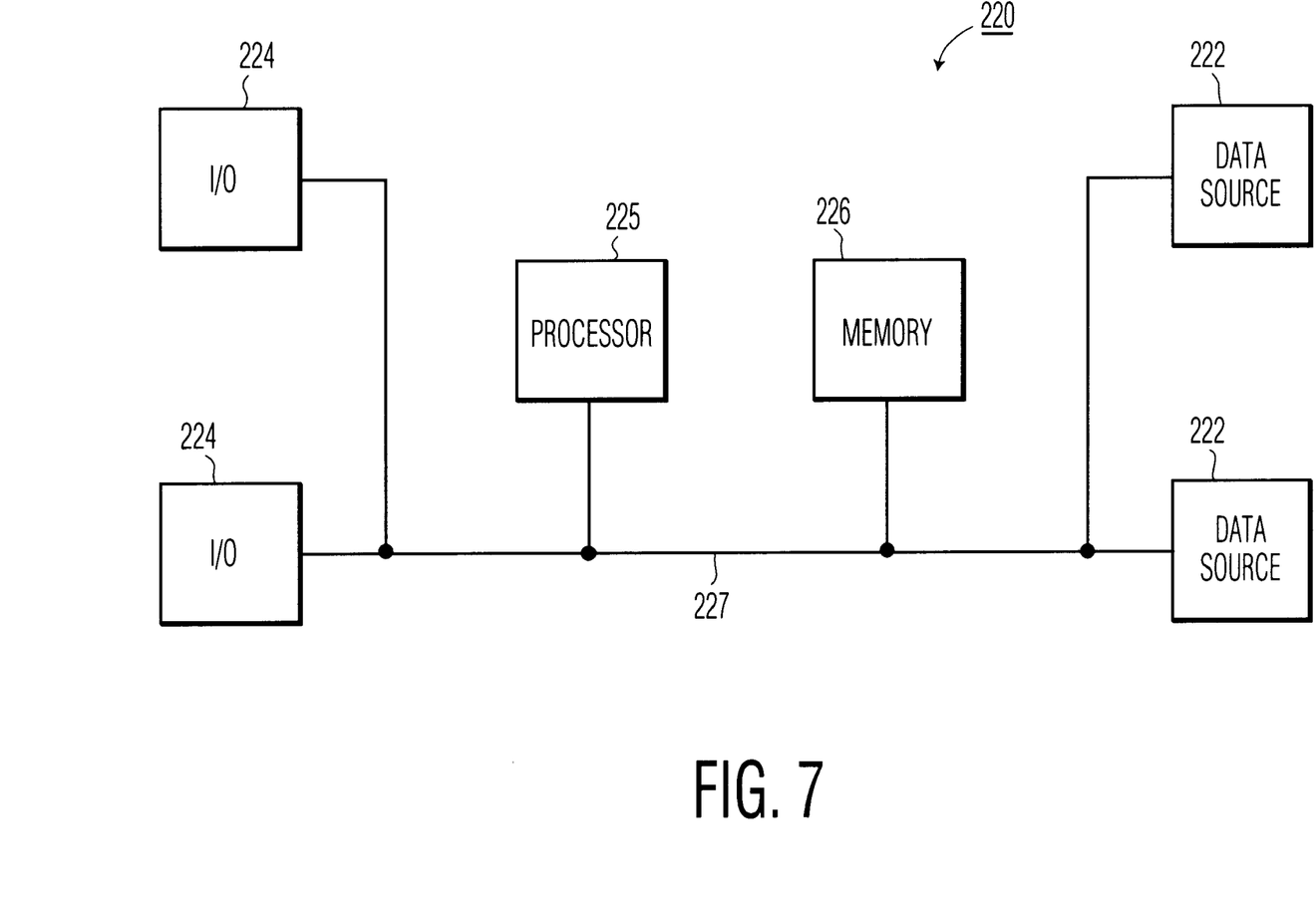
FIG. 7 is a block diagram of an exemplary computer system in accordance with one aspect of the invention.

FIG. 7 shows a data processing system 220 in which the data-analysis unit 24 may be implemented. The system 220 includes one or more input sources 222, one or more input/output devices 224 (e.g., a display, a mouse and a printer), a processor 225 and a memory 226. The input source(s) 222 may represent a direct link to the signal-collecting unit 20 and/or may represent one or more network connections for receiving data from a server or servers over, e.g., a global computer communications network such as the Internet, a wide area network, a metropolitan area network, a local area network, a terrestrial broadcast system, a cable network, a satellite network, a wireless network, or a telephone network, as well as portions or combinations of these and other types of networks.

The input/output devices 224, processor 225 and memory 226 communicate over a communication medium 227. The communication medium 227 may represent, e.g., a bus, a communication network, one or more internal connections of a circuit, circuit card or other device, as well as portions and combinations of these and other communication media. Input data from the source(s) 222 is processed in accordance with one or more software programs executed by processor 225 in order to determine the film's thickness or other properties as discussed above. The software programs may be stored in the memory 226 or read/downloaded from a memory medium such as a CD-ROM or floppy disk. In other embodiments, hardware circuitry may be used in place of, or in combination with, software instructions.

It should be understood that the particular configuration of system 220 as shown in FIG. 7 is by way of example only. Those skilled in the art will recognize that the invention can be implemented using a wide variety of alternative system configurations.

Still other embodiments are within the scope of the invention. Other measurements can be performed using the coherent X-rays 14 described above. For example, referring to FIG. 6, in an Impulsive Stimulated Thermal Scattering ("ISTS") measurement two x-ray excitation pulses 111, 111' are overlapped on a surface 112 of a sample 114 to interfere and form an excitation pattern 113 that launches multiple acoustic waves within the sample 114. Each x-ray excitation pulse is formed by an optical pulse as described above, and is supplied to the sample 114 by a separate fiber 130', 130". The excitation pattern features alternating regions of "light" 113A (constructive interference) and "dark" 113B (destructive interference). The light 113A regions are absorbed by the sample, causing it to expand rapidly underneath. This process launches acoustic waves having a wavelength that matches the light and dark regions of excitation pattern. The acoustic waves cause the sample's surface to ripple. A probe beam 115 impinges the sample 112 and reflects off the surface to form a reflected beam 115'. Portions of probe beam 115 diffract off the surface ripple to form a pair of diffracted beams 116, 116'. A detector 117 collects one of the diffracted beams 116 or 116', and in response generates a signal waveform. An analyzer (not shown in the figure) connected to the detector 117 receives the signal waveform and processes it by taking a Fourier transform to determine a frequency of oscillation of the acoustic waves. The frequency of oscillation can then be analyzed to determine a thickness of a film in the sample.

Figure 6:
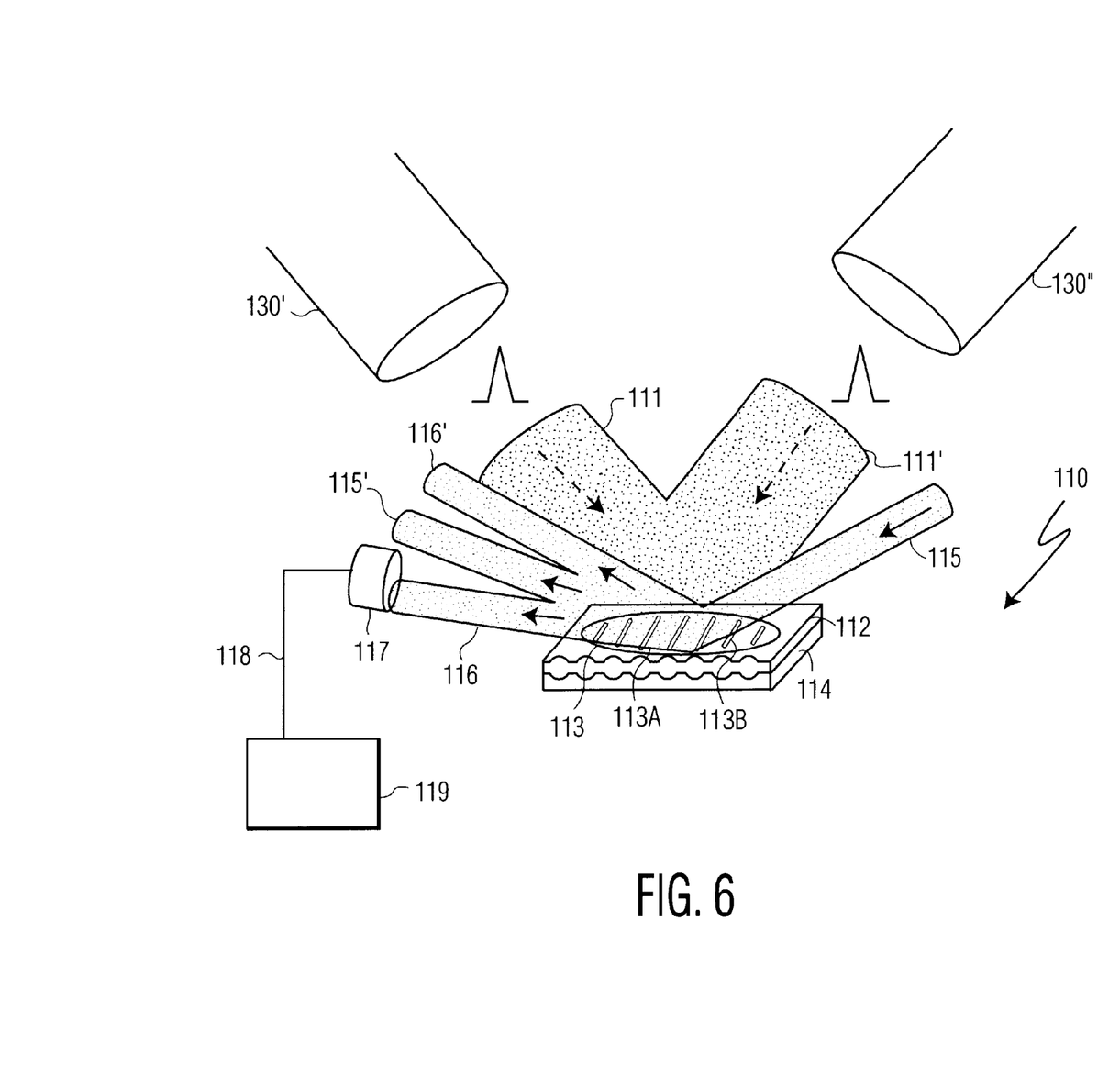
FIG. 6 is a schematic view of a four-wave mixing measurement using coherent x-ray beams.

The probe beam 115 generates an x-ray probe beam as described above. An x-ray probe beam has certain advantages compared to an optical probe beam. For example, an x-ray probe wavelength will be diffracted off the short wavelength of the acoustic waves more effectively than an optical probe beam, thereby increasing the magnitude of the signal beam. Generally, the detector 117 does not need high bandwidth because the probe beam 115 is a variably delayed probe pulse, not a continuous wave (cw) beam. Accordingly, in a single shot, the detector 117 measures the amount of diffracted signal (i.e., diffracted beams 116 or 116') but not the time-dependence of the signal. The time-dependence is determined by varying the probe delay time and measuring the diffracted signal intensity versus delay time.

Similar ISTS measurement methods using optical excitation pulses are described, for example, in issued U.S. Pat. No. 5,633,711 (entitled MEASUREMENTS OF MATERIAL PROPERTIES WITH OPTICALLY INDUCED PHONONS); U.S. Pat. No. 5,546,811 (entitled OPTICAL MEASUREMENT OF STRESS IN THIN FILM SAMPLES); and U.S. Pat. No. 5,812,261 (entitled METHOD AND DEVICE FOR MEASURING THE THICKNESS OF OPAQUE AND TRANSPARENT FILMS), the contents of which are incorporated herein by reference.

ISTS performed with x-ray beams has the advantage over conventional, optical ISTS in that the light and dark regions of the excitation pattern can be formed very close together due to the short wavelength of the interfering x-ray pulses. This, in turn, generates acoustic waves with relatively short wavelengths and high acoustic frequencies compared to those generated with optical means. Acoustic waves with these properties are highly sensitive to thickness changes in the measured film, especially for very thin layers.

Still other embodiments are within the scope of the claims. For example, coherent x-rays may be generated directly from an x-ray laser and used for the fluorescence and ISTS measurements described above. Other types of metrology using x-ray beams could be undertaken. For example, time-resolved measurements (e.g. of x-ray diffraction) could be made, using either x-ray pulses or optical pulses in the visible or other spectral regions. Other acoustic measurements, such as generating and measuring "acoustic echoes", could be performed with the coherent x-ray pulses. The spacing between the acoustic echoes can be analyzed to determine the thickness of a film in the sample.

While the present invention has been described above in terms of specific embodiments, it is to be understood that the invention is not intended to be confined or limited to the embodiments disclosed herein. On the contrary, the present invention is intended to cover various structures and modifications thereof included within the spirit and scope of the appended claims.

What is claimed is:

1. A method for measuring a property of a sample, comprising:

generating an optical pulse;

focussing the optical pulse onto or in a material to generate a coherent x-ray pulse;

delivering the coherent x-ray pulse to a region on the sample to generate a signal;

detecting the signal to generate an electrical signal; and analyzing the electrical signal to determine the property of the sample, wherein the property is selected from the group consisting of thickness, composition, uniformity, density, sound velocity, layer adhesion quality and refractive index.

2. The method of claim 1, wherein the generating step further includes generating an optical pulse that has duration of 5 picoseconds or less.

3. The method of claim 2, wherein the generating step further includes generating the optical pulse with a laser comprising titanium:sapphire.

4. The method of claim 1, wherein the focussing step further includes focussing the optical pulse into a gas-containing container.

5. The method of claim 1, wherein the focussing step further includes focussing the optical pulse into an optical fiber.

6. The method of claim 5, wherein the fiber comprises a gas-containing region.

7. The methods of claim 5 and 6, wherein the gas comprises one of argon, helium, hydrogen, or nitrogen.

8. The method of claim 1, wherein the focussing step further includes generating a coherent x-ray pulse having a duration that is less than twice the duration of the optical pulse.

9. The method of claim 1, wherein the delivering step further includes delivering the coherent x-ray pulse to the sample to initiate fluorescence.

10. The method of claim 9, wherein the detecting step further includes detecting the x-ray-induced fluorescence to generate an electrical signal having properties determined by the fluorescence intensity and photon energy.

11. The method of claim 10, wherein the analyzing step further includes analyzing the electrical signal to determine at least one of the fluorescence intensity or photon energy.

12. The method of claim 11, wherein the fluorescence intensity is compared to a mathematical model that relates fluorescence intensity and thickness to determine a film thickness of the sample.

13. The method of claim 11, wherein the fluorescence energy is compared to a mathematical model that relates fluorescence energy and composition to determine a film composition of the sample.

14. The method of claim 1, wherein the delivering step further includes delivering at least one x-ray beam to the sample to generate an acoustic wave or pulse.

15. The method of claim 14, further including the step of irradiating the acoustic wave or pulse with an optical or x-ray probe beam to generate the signal beam.

16. The method of claim 15, wherein a portion of the acoustic wave or pulse propagates in the plane of the sample.

17. The method of claim 16, wherein a portion of the probe beam is diffracted from the acoustic wave or pulse.

18. The method of claim 17, wherein the detecting step further includes measuring a diffracted portion of the probe beam, and the analyzing step further includes determining a frequency from the diffracted portion of the probe beam.

19. The method of claim 18, wherein the analyzing step further includes analyzing the frequency with a mathematical model to determine a film thickness of the sample.

20. The method of claim 15, wherein a portion of the acoustic wave or pulse propagates through the plane of the sample.

21. An apparatus for measuring at least one property a sample, comprising:
a coherent x-ray generator arranged to irradiate a region of the sample;
a detector arranged to detect a signal from the region of the sample and to generate an electrical signal; and
an analyzer arranged to determine the property of the sample in accordance with the electrical signal,
wherein the property is selected from the group consisting of thickness, composition, uniformity, density, sound velocity, layer adhesion quality and refractive index.

22. The apparatus of claim 21, wherein the generator comprises a pulsed laser that is capable of generating an optical pulse that has duration of 5 picoseconds or less.

23. The apparatus of claim 22, wherein the pulse laser comprises titanium:sapphire.

24. The apparatus of claim 21, wherein the generator comprises an optical fiber.

25. The apparatus of claim 24, wherein the optical fiber comprises a gas-containing region.

26. The apparatus of claim 25, wherein the gas-containing region contains at least one of argon, helium, hydrogen, or nitrogen.

27. The apparatus of claim 22, wherein the generator generates the coherent x-ray pulse having a duration that is less than twice the duration of the optical pulse.

28. The apparatus of claim 21, wherein the signal is based on a fluorescence response of the sample.

29. The apparatus of claim 28, wherein the detector is capable of detecting x-ray-induced fluorescence to generate the electrical signal having properties determined by the fluorescence intensity and photon energy.

30. The apparatus of claim 29, wherein the analyzer is capable of analyzing the electrical signal to determine at least one of the fluorescence intensity or photon energy.

31. The apparatus of claim 30, wherein the fluorescence intensity is compared to a mathematical model that relates fluorescence intensity and thickness to determine the thickness of at least one film layer of the sample.

32. The apparatus of claim 21, wherein the generator is capable of delivering at least one x-ray beam to the sample to generate an acoustic wave or pulse.

33. The apparatus of claim 32, wherein the analyzer is capable of analyzing time-dependent values related to the signal to determine the thickness of at least one film layer of the sample.

34. A memory medium including code for a measurement system that uses coherent x-rays to generate fluorescence in a sample, the code comprising:
code to receive a signal based upon a coherent x-ray initiated fluorescence from the sample;
code to determine a value of the signal;
code to compare the value to a predetermined mathematical model that relates the value to a physical property of the sample.

35. The memory medium according to claim 34, wherein the value relates to fluorescence intensity or fluorescence energy of the signal.

36. The memory medium according to claim 34, wherein the predetermined mathematical model includes at least one correlation plot which is generated in accordance with a plurality of calibration samples.

37. The memory medium according to claim 36, wherein the physical property is a thickness of the sample.

* * * * *